United States Patent
Tóth et al.

[11] 3,978,075
[45] Aug. 31, 1976

[54] SUBSTITUTED CARBAMOYL BENZIMIDAZOLE DERIVATIVES WITH ANTIFUNGAL PROPERTIES

[75] Inventors: Géza Tóth; István Tóth, both of Budapest, Hungary

[73] Assignee: Chinoin Gyogyszer-es Vegyeszeti Termekek Gyara RT, Budapest, Hungary

[22] Filed: Apr. 25, 1975

[21] Appl. No.: 571,763

[30] Foreign Application Priority Data
May 2, 1974 Hungary............................ CI 1473

[52] U.S. Cl............................. 260/309.2; 424/273
[51] Int. Cl.²...................................... C07D 405/12
[58] Field of Search.................. 260/309.2; 424/273

[56] References Cited
UNITED STATES PATENTS

| | | | |
|---|---|---|---|
| 3,401,173 | 9/1968 | Chow et al. | 260/309.2 |
| 3,578,676 | 5/1971 | Dunn | 260/309.2 |
| 3,673,210 | 6/1972 | Daum et al. | 260/309.2 |
| 3,694,455 | 9/1972 | Dunn | 260/309.2 |

FOREIGN PATENTS OR APPLICATIONS

| | | | |
|---|---|---|---|
| 809,234 | 6/1974 | Belgium | 260/309.2 |
| 2,046,114 | 2/1971 | France | 260/309.2 |
| 1,072,735 | 6/1967 | United Kingdom | 260/309.2 |

OTHER PUBLICATIONS
Grier Chem. Abst. 1970, vol. 72, No. 132730j.
Osieka et al. Chem. Abst. 1973, vol. 79, No. 137151a.
Smith, Kline and French Chem. Abst. 1969, vol. 70, No. 87805h.

*Primary Examiner*—Natalie Trousof
*Attorney, Agent, or Firm*—Karl F. Ross; Herbert Dubno

[57] ABSTRACT

Antifungal substituted carbamoyl benzimidazole compounds of the formula

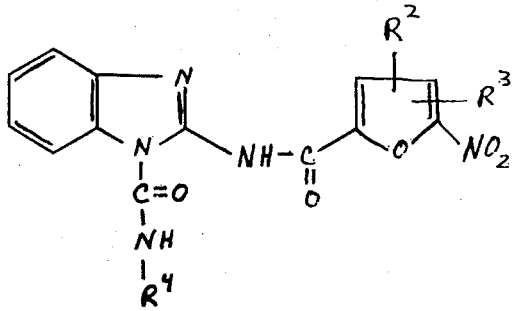

wherein $R^2$ and $R^3$ are hydrogen or alkyl and $R^4$ is aryl, alkyl or cycloalkyl. The compounds can be used as seed treatment.

8 Claims, No Drawings

SUBSTITUTED CARBAMOYL BENZIMIDAZOLE DERIVATIVES WITH ANTIFUNGAL PROPERTIES

This invention relates to new benzimidazole derivatives, and the salts thereof, and to the use of the same.

According to an aspect of the present invention, there are provided compounds of the formula I

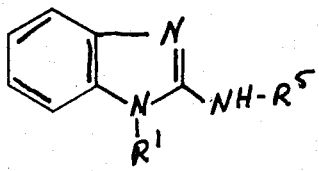

(I)

and salts thereof, wherein
$R^1$ is —CO—NH-$R^4$,
$R^4$ is substituted or unsubstituted aryl, alkyl, or cycloalkyl; and
$R^5$ is a group of the formula II

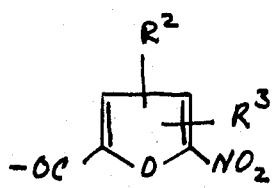

(II)

wherein
$R^2$ and $R^3$ stand for hydrogen or alkyl.

The term "alkyl group" as used herein means straight or branched chained saturated aliphatic hydrocarbon groups, having 1–6 carbon atoms (e.g. methyl, ethyl, n-propyl, isobutyl, etc.). The term "aryl group" is used herein to refer to aromatic groups, having 7–10 carbon atoms (e.g. phenyl or naphthyl), which may be substituted by one or more substituents selected from the group consisting of halogen, alkyl, and alkoxy. Preferred substituted aryl groups are the 3-chlorophenyl and 3,4-dichlorophenyl groups. The term "cycloalkyl group" is used herein to identify cycloalkyl groups having 3–6 carbon atoms (preferably cyclopropyl, cyclobutyl, cyclopentyl and cyclohexyl).

The salts of the compounds of the formula I may be formed with inorganic or organic acids, e.g. hydrochlorides, hydrobromides, sulphates, acetates, formiates, lactates, tartarates, etc. The salts to be used in therapy must be formed with pharmaceutically acceptable acids.

Particularly preferred derivatives of the formula I are the following compounds:
1-(3,4-dichlorophenyl-carbamoyl)-2-)5'-nitro-furyl-2'-carbonyl-amino)-benzimidazole;
1-cyclohexylcarbamyl-2-(5'-nitro-furyl-2'-carbonyl-amino)-benzimidazole;
1-n-butylcarbamoyl-2-(5'-nitro-furyl-2'-carbonyl-amino)-benzimidazole;
1-phenylcarbamoyl-2-(5'-nitro-furyl-2'-carbonyl-amino)-benzimidazole;
1-propylcarbamoyl-2-(5'-nitro-furyl-2'-carbonyl-amino)-benzimidazole;
1-[(3'-chlorophenyl-carbamoyl)-2-(5'-nitro-furyl-2'-carbonyl-amino)]-benzimidazole; and
1-methylcarbamoyl-2-(5'-nitro-furyl-2'-carbonyl-amino)-benzimidazole.

According to a further feature of the present invention, there is provided a process for the preparation of compounds of the formula I and salts thereof, wherein $R^1$ and $R^5$ have the same meaning as stated above, which comprises a. reacting a compound of the formula IV

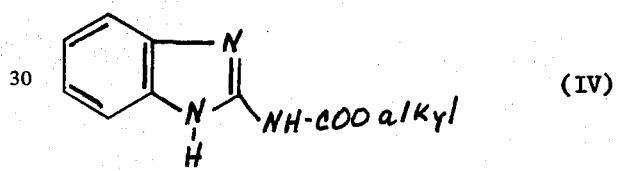

(IV)

or V

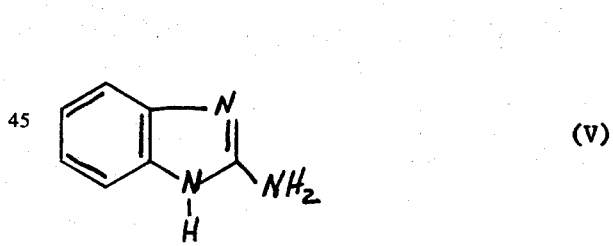

(V)

with a reactive acid derivative containing a group of the formula II; or b. reacting a compound of the formula VI

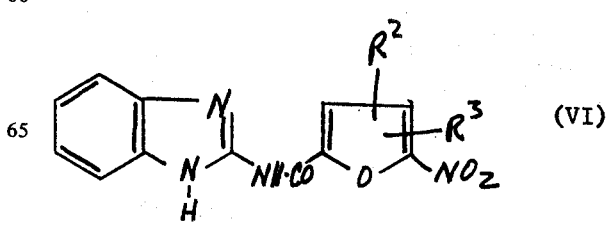

(VI)

with a reactive acid derivative — preferably with an isocyanate containing the group of the formula III; and if desired, converting a compound of the formula I thus obtained into its salt, or setting free the compound of formula I from its salt.

According to a preferred embodiment of process (a) a compound of the formula IV or V is reacted with 5-nitro-2-furoyl -carboxylic acid, or with a halide or ester thereof preferably with 5-nitro-2-furoyl-carboxylic acid-chloride.

The process is carried out preferably in an organic solvent in the presence of a basic substance. If a carboxylic acid ester is used, it is preferred to remove the alcohol formed continuously. If the reaction is carried out by using the free acid it is preferable to carry out the reaction in the presence of a condensing agent (e.g. dicyclohexyl-carbodiimide) in dimethylformamide.

According to a preferred embodiment of process (b), the compound of the formula VI is reacted with an alkyl, cycloalkyl or arylisocyanate.

The arylisocyanate may bear optionally one or more alkyl or halogen substituents, e.g. methyl, ethyl, propyl, chloro-, bromo-, bromide, or iodine substituents.

The compounds of the formula I may be converted into their salts in a conventional manner preferably by reacting the compound of the formula I with an approximately equimolar amount of the acid in the presence of an organic solvent.

The compounds of the formula I, and their salts possess valuable fungicidal properties and may be used in human and veterinary therapy as well as in agriculture.

According to a further feature of the present invention there are provided pharmaceutical compositions for use in both human and veterinary therapy comprising at least one compound of the formula I or a salt thereof in admixture with suitable pharmaceutically acceptable solid or liquid carriers or diluents.

The pharmaceutical compositions may be finished in the form of solutions, suspensions, emulsions, tablets, dragees, powder mixtures, ointments or granules. The compositions contain conventional carriers used in pharmacy e.g. starch, talc, calcium, carbonate, magnesium stearate, water, polyalkylene glycols, etc.

According to a still further feature of the present invention, there are provided disinfectants, comprising at least one compound of the formula I, or salts thereof. The said disinfectants are preferably formulated in the form of aqueous solutions. such aqueous solutions containing about 1% of a compound of the formula I or a salt thereof are particularly suitable for the disinfecting of swimming pools, or other large objects subject to fungal infections.

According to a further feature of the present invention, there are provided pesticidal compositions, comprising at least one compound of the formula I, or a salt thereof in admixture with suitable inert, solid or liquid carriers or diluents.

The said pesticides may be finished as dusting powders, sprays, granules, emulsifiable concentrates, etc. The compositions contain carriers and diluents generally used in the formulation of pesticides. The composition may also contain surface-active agents or other additives.

The pesticides contain from about 0.001 % to about 95 % of the active ingredient of the formula I. While the diluted compositions suitable for direct use, may contain generally from about 0.001 to about 1% of the active ingredient, the concentrates may contain from about 20 % to about 80 % of active ingredients.

The pesticidal compositions of the present invention exhibit particularly strong activity against fungi belonging to the Fusarium, Basidiomycetes or Helminthosporium family. The compositions are particularly effective with preferably--; wheat plants against Tillethia tritici, with rye plants against Fusarium nivale, and with sugar, beet plants against Cercospore beticola. The compositions may be advantageously used for seed dressing.

According to a still further feature of the present invention, there are provided cosmetic compositions comprising as active ingredient at least one compound of the formula I, or a salt thereof.

Further details of the present invention are to be found in the Examples.

EXAMPLE 1

19.1 g. (0.1 mole) of (2-carbomethoxy-amino)-benzimidazole are suspended in 250 ml. of dioxane, whereupon 10 g. of triethylaminne are added at 50°–60°C. Thereafter 17.5 g. (0.1 mole) of 5-nitro-2-furane-carboxylic acid chloride are added within 30 minutes. The reaction mixture warms up. The mixture is refluxed for 3 hours, whereupon it is stirred at 15°C for 0.5 hours and washed with water. Thus 25.2 g. of 1-(5-nitrofuryl-2-carbonyl)-2-carbomethoxy-amino-benzimidazole are obtained. Mp.: 175°C (decomposition).

EXAMPLE 2

13.3 g. (0.1 mole) of 2-amino-benzimidazole are suspended in 250 ml. of dioxane, whereupon 10 g. of triethylamine are added. The mixture is heated to 60°C, whereupon at this temperature 17.5 g. (0.1 mole) of 5-nitro-2-furane-carbonyl chloride are added. The reaction mixture is stirred at 60°C for 2 hours, whereupon it is cooled to 15°C. Thus 25.5 g. of N-(2'-benzimidazolyl)-5-nitro-furane carboxylic acid amide are obtained. Mp.: 240°–242°C.

EXAMPLE 3

6.8 g. (25 millimole) of N-(2'-benzimidazolyl)-5-nitro-furane-carboxylic acid amide are stirred with 60 ml. of chloroform, whereupon to the solution 4.8 g. (25 millimoles) of 3,4-dichloro-phenyl-isocyanate are added. The reaction mixture is stirred at room temperature for 6 hours, whereupon it is allowed to stand overnight, and the precipitated crystals are filtered off. Thus 1-(3,4-dichloro-phenyl-carbamoyl-2-(5'-nitrofuryl-2-carbonyl-amino)-benzimidazole are obtained in the form of yellow crystals melting at 235°–237°C.

EXAMPLE 4

6.8 g. (25 millimoles) of N-(2'-benzimidazolyl)-5-nitro-furane-carboxylic acid amide are stirred in 60 ml. of chloroform, whereupon 3.2 g. (25 millimoles) of cyclohexylisocyanate are added. The reaction mixture is stirred for 6 hours, allowed to stand for an hour, the precipitated product is filtered off and washed with a small amount of chloroform. Thus 8.0 g. of 1-cyclohexyl-carbamoyl-2-(5'-nitro-furyl-2'-carbonyl-amino)-benzimidazole are obtained. Mp.: 208°–213°C /yellow crystals/.

EXAMPLE 5

6.8 g. (25 millimoles) of N-/2'-benzimidazolyl)-5-nitro-furane-carboxylic acid amide are stirred in 60 ml.

of chloroform, whereupon 2.48 g. (25 millimoles) of butyl-isocyanate are added, and the reaction mixture is stirred for 6 hours. The reaction mixture is allowed to stand overnight, the precipitated product is filtered off and washed with chloroform. Thus 8.05 g. of 1-n-butyl-carbamoyl-2-(5-nitro-furyl-2'-carbonyl-amino)-benzimidazole are obtained. The melting point of the yellow crystals amounts to 258°–259°C.

EXAMPLE 6

6.8 g. (25 millimoles) of N-(2'-benzimidazolyl)-5-nitro-furane-carboxylic acid amide are suspended in 60 ml. of chloroform, whereupon 3.0 g. (25 millimoles) of phenylisocyanate are added. The reaction mixture is stirred for 6 hours at room temperature, whereupon the precipitated product is filtered off and washed with a small amount of chloroform. Thus 8.6 g. of 1-phenyl-carbamoyl-2-(5'-nitro-furyl-2'-carbonyl-amino)-benzimidazole are obtained. Mp.: 235°–255°C (yellow crystals).

EXAMPLE 7

6.8 g. (25 millimoles) of N-(2'-benzimidazolyl)-5-nitro-furane-carboxylic acid amide are stirred in 60 ml. of chloroform, whereupon 2.15 g. (25 millimoles) of propyl-isocyanate are added. The reaction mixture is stirred at room temperature for 6 hours, whereupon it is filtered off and washed with a small amount of chloroform. Thus 8.3 g. of 1-propyl-carbamoyl-2-[5'-nitro-furyl-2'-carbonyl-amino]-benzimidazole are obtained. Mp.: 260°–262°C (yellow crystals).

EXAMPLE 8

6.8 g. (25 millimoles) of N-(2'-benzimidazolyl)-5-nitro-furane-carboxylic acid amide are stirred in 60 ml. of chloroform. whereupon 3.8 g. (25 millimoles) of 3-chlorophenylisocyanate are added. The reaction mixture is stirred at room temperature for 6 hours, filtered and washed with a small amount of chloroform. Thus 9.9 g. of 1)-3-chlorophenyl-carbamoyl/-2-5''-nitro-furyl-2''-carbonyl-amino/-benzimidazole are obtained. The melting point of the yellow crystals amounts to 259°–260°C.

EXAMPLE 9

6.8 g. (25 millimoles) of N-(2'-benzimidazolyl)-5-nitro-furane-carboxylic acid amide are stirred with 60 ml. of chloroform, whereupon 1.5 g. (25 millimoles) of methylisocyanate are added. The reaction mixture is stirred at room temperature for 6 hours, whereupon the precipitated product is filtered off, and washed with a small amount of chloroform. Thus 7.6 g. of 1-methyl-carbamoyl-2-(5'-nitro-furyl-2'-carbonyl-amino)-benzimidazole are obtained. Mp.: 267°–269°C. (yellow crystals).

What we claim is:
1. A compound of the formula

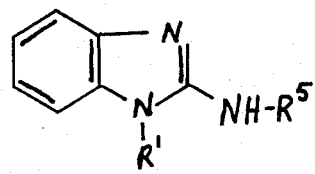

and antifungal salts thereof wherein $R^1$ is —CO—NH—$R^4$ and $R^5$ is a group with the formula

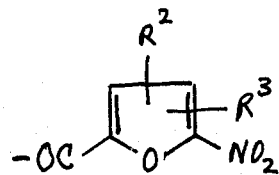

in which $R^2$ and $R^3$ are each hydrogen or $C_1$–$C_6$ alkyl, $R^4$ being $C_1$–$C_6$ alkyl, phenyl, naphthyl, $C_7$ to $C_{10}$ aryl substituted with halogen, $C_1$–$C_6$ alkyl or $C_1$ to $C_6$ alkoxy, or $C_3$–$C_6$ cycloalkyl.

2. A compound as defined in claim 1 of the formula 1-(3,4-dichlorophenyl-carbamoyl)-2-(5'-nitro-furyl-2'-carbonyl-amino)-benzimidazole.

3. A compound as defined in claim 1 of the formula 1-cyclohexylcarbamoly-2-(5'-nitro-furyl-2'-carbonyl-amino)-benzimidazole.

4. A compound as defined in claim 1 of the formula 1-n-butylcarbamoyl-2-(5'-nitro-furyl-carbonylamino)-benzimidazole.

5. A compound as defined in claim 1 of the formula 1-phenylcarbamoyl-2-(5'-nitro-furyl-2'-carbonyl-amino)-benzimidazole.

6. A compound as defined in claim 1 of the formula 1-propylcarbamoyl-2-(5'-nitro-furyl-2'carbonyl-amino)-benzimidazole.

7. A compound as defined in claim 1 of the formula 1-(3-chlorophenyl-carbamoyl)-2(5'-nitro-furyl-2'-carbonyl-amino)-benzimidazole.

8. A compound as defined in claim 1 of the formula 1-methylcarbamoyl-2-(5'-nitro-furyl-2'carbonyl-amino)-benzimidazole.

* * * * *